United States Patent [19]

Misaki et al.

[11] Patent Number: 4,769,363

[45] Date of Patent: Sep. 6, 1988

[54] BETA-GLUCAN

[75] Inventors: Akira Misaki; Yoshiaki Sone, both of Osaka; Mikihiko Yoshida; Kanou Takeuchi, both of Okayama, all of Japan

[73] Assignee: Kabushiki Kaisha Hayashibara Seibutsu Kagaku Kenkyujo, Okayama, Japan

[21] Appl. No.: 708,057

[22] Filed: Mar. 4, 1985

[30] Foreign Application Priority Data

Mar. 8, 1984 [JP] Japan .................... 59-44573

[51] Int. Cl.$^4$ ........................ A61K 31/70; C07H 15/04
[52] U.S. Cl. ........................ 514/54; 536/1.1; 536/120; 514/23
[58] Field of Search .................. 536/1.1, 120; 514/23, 514/54

[56] References Cited

U.S. PATENT DOCUMENTS 4,202,966  5/1980  Misaki et al. .................. 536/1.1
4,306,059 12/1981  Yokobayashi et al. ........... 536/1.1
4,430,322  2/1984  Stoudt et al. .................. 536/1.1
4,603,197  7/1986  Kadoya et al. ................. 536/1.1

OTHER PUBLICATIONS

Cram et al., *Organic Chemistry*, 2nd Ed., 1964, pp. 300, 416 and 633–634.

*Primary Examiner*—J. R. Brown
*Assistant Examiner*—Elli Peselev
*Attorney, Agent, or Firm*—Browdy and Neimark

[57] ABSTRACT

A novel beta-1,3-glucan (ganoderan) is produced by culturing a microorganism of genus Ganoderma. Ganoderan is composed of a backbone structure of beta-1,3-linked D-glucopyranose residues bearing, at some of the C-6 positions, side chains of single beta-1,6-linked D-glucopyranose residue, and, at some of the C-2 positions, side chains of another type wherein 2-4 D-glucopyranose residues are linked via beta-1,4-linkage. Hydrogenation of ganoderan leads to the formation of a polyol-type ganoderan. Intact- and polyol-type ganoderans both having a strong antioncotic activity. They are usable in chemicals, food products, pharmaceuticals, etc.

3 Claims, 1 Drawing Sheet

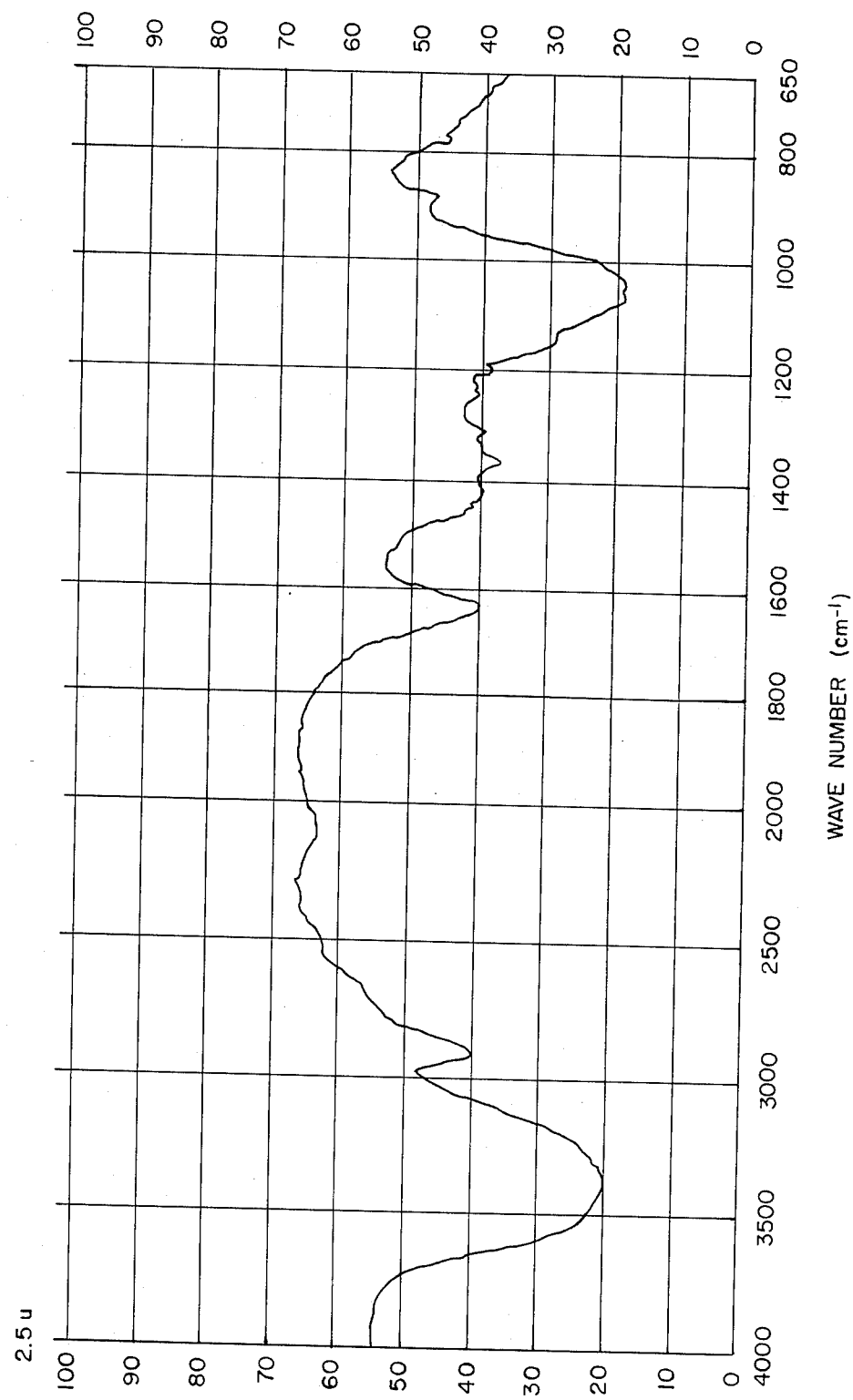

BETA-GLUCAN

FIELD OF THE INVENTION

The present invention relates to a novel beta-glucan, as well as to its production and uses.

DEFINITION

The "part(s)" used herein is indicated by weight.

BACKGROUND OF THE INVENTION

Certain beta-glucans are found to exhibit significant physiological activities, e.g. hypoglycemic-, hypocholesterolemic- and antioncotic activities via the cellular immune system. Thus, they have drawn attentions as medicine or material therefor.

Examples of pharmaceutically significant beta-glucans which have a use as antioncotic for malignant tumors are "Pachyman" derived from the fruit body of *Poria cocos* Wolf, as reported in H. Saito et al., *Agricultural and Biological Chemistry*, Vol. 32, 1261–1269 (1968); "Lentinan" derived from the fruit body of *Lentinus edodes* Berk, as reported in T. Sasaki et al., *Carbohydrate Research*, Vol. 47, pp. 90–104 (1976); "Schizophillan" derived from a culture of *Schizophillum commune*, as reported by K. Tabata et al., *Carbohydrate Research*, Vol.89, pp.121–135 (1981); and a beta-glucan derived from the fruit body of *Auricularia auricula-judae* ("kikurage", an edible mushroom), as reported in A. Misaki et al., *Carbohydrate Research*, Vol.92, pp.115–129 (1981). These beta-glucans bear in common a backbone structure of beta-1,3-linked D-glucopyranose residues with beta-1,6-linked side chains at some of the C-6 positions, and are used in pharmaceuticals as antioncotic.

BRIEF DESCRIPTION OF THE DRAWING

The single FIGURE indicates the infrared spectrum of a purified beta-glucan of the present invention.

DETAILED DESCRIPTION OF THE INVENTION

We investigated beta-glucans usable in various industries, food industry, chemical industry, etc., as well as in the pharmaceutical industry. As the result, we found in a culture of a Ganoderma microorganism a beta-glucan having a novel structure bearing a backbone of beta-1,3-linked D-glucopyranose residues with, at some of the C-6 positions, side chains of single D-glucopyranose residue and, at some of the C-2 positions, side chains of another type wherein 2 to 4 D-glucopyranose residues are linked via beta-1,4 linkages.

Although in many articles have been reported glucans produced by Ganoderma microorganisms, most of these were found in the extracts of their fruit bodies. For example, T. Usui et al., *Carbohydrate Research*, Vol.115, pp.273–280 (1983) reports that a beta-1,3 glucan bearing side chains of single D-glucopyranose residue per three D-glucopyranose residues of the backbone was obtained by extracting the fruit body of *Ganoderma applanatum* in hot water. T. Ukai et al., *Carbohydrate Research*, Vol.105, pp.237–245 (1982) reports that a beta-1,3 glucan having side chains of single D-glucopyranose residue per thirty D-glucopyranose residues of the backbone was obtained by extracting the fruit body of *Ganoderma japonicum* Lloyd in 1N caustic soda, T. Miyazaki et al., *Carbohydrate Research*, Vol.109, pp.290–294 (1982) reports that a heteroglucan containing fucose, xylose and mannose in a mole ratio of 1:1:1 was obtained by extracting the fruit body of *Ganoderma lucidum* in 0.1M caustic soda.

These are, however, distinct from the beta-glucan of the present invention. We named our novel beta-glucan "Ganoderan".

The following properties confirm that ganoderan is a novel beta-glucan:

(1) Homogeneity

Homogenous on ultracentrifugation or electrophoresis.

(2) Elemental analysis: $C=44.5\%$, $H=6.1\%$, $N<0.1\%$, ash $<0.001\%$ (observed). $C=44.4\%$, $H=6.17\%$ (calculated), (3) Solubility Freely soluble in 25° C. water on freeze-drying, but scarcely soluble on heat-drying.

Freely soluble in 0.5N caustic soda, and dimethyl sulfoxide. Insoluble in organic solvents, e.g. methanol, ethanol, acetone, chloroform, ethyl acetate, etc.

(4) Physical properties

White or pale yellow.

Tasteless and odorless.

Neutral or slightly acidic in aqueous solution.

(5) Coloring reactions

Anthrone-sulfuric acid reaction: positive

Phenol-sulfuric acid reaction: positive

Carbazole reaction: negative

Iodine reaction: negative.

(6) Infrared spectrum

As shown in the FIGURE, the infrared spectrum obtained by the KBr tablet method shows a strong absorption by hydroxyl groups at around 3,200–3,600 $cm^{-1}$, and an absorption specific to betaglucosyl linkage at around 890 $cm^{-1}$.

(7) Sugar component

Ganoderan was completely hydrolyzed in an inorganic or organic acid by one of the following methods: a method wherein ganoderan was allowed to stand in 72% sulfuric acid at room temperature for five minutes, diluted seven-times with water, and kept at 100° C. for four to five hours; a method wherein ganoderan was allowed to stand in 90–100% formic acid at 100° C. for ten hours; or a method wherein ganoderan was heated in 2M trichloroacetic acid at 100° C. for six hours. The resultant hydrolysate was nentralized, and its sugar component was analyzed by paper-chromatography and glucose oxidase-peroxidase method. After converting into alditol acetate the sugar component was gas-chromatographed. The results show that the sugar component was D-glucose.

(8) Mode of linkage (i) Ganoderun was dissolved in dimethyl sulfoxide, and converted into the methyl derivative by Hakomori's method using methylsulphonyl carbanion and methyl iodide, followed by acid-hydrolysis of the methyl derivative. The resultant methylated sugars were converted into alditol acetates which were then identified, and quantitatively analyzed with gas-chromatography and mass-spectrometry. The mole ratios of the alditol acetates to 1.0 mole of 2,3,4,6-tetra-O-methyl-D-Glucose are as follows: 2,4,6-tri-O-methyl-D-glucose, about 1.5–2.0 moles; 2,3,6-tri-O-methyl-D-glucose, about 0.2–0.6 moles; 2,4-di-O-methyl-D-glucose, about 0.8–1.0 moles; and 4,6-di-O-methyl-D-glucose, about 0.1–0.2 moles.

(ii) The specific rotation, $[\alpha]_D^{25}$, of 0.2% ganoderan in 0.5N aqueous caustic soda solution was approximately plus 10 degrees; and that of the methylated ganoderan in 0.15% chloroform was approximately minus 40 degrees.

(iii) Ganoderan was completely oxidized with 0.05M sodium metaperiodate, and then reduced with sodium borohydride. The resultant polyol-type ganoderan was hydrolyzed in 0.5M sulfuric acid at 100° C. for 2–3 hours to obtain a mixture containing glucose, glycerol and a small amount of erythritol.

The mixture was reduced, converted into acetyl derivative, and gas-chromatographed to obtain a mole ratio of glycerol, glucose and erythritol of 0.3–0.4:1.0:0.03.

Separately, the polyol-type ganoderan was kept at 90°–100° C. for 1–2 hours in 0.05–0.1M sulfuric acid to obtain, as well as glycerol and erythritol, an insoluble substance. Hydrolysis of the insoluble substance gave D-glucose as sole product, while hydrolysis of a methylated polyol-type ganoderan gave a substantial amount of 2,4,6-tri-O-methyl-D-glucose. By exposure to the action of exo-beta-1,3 glucanase, only D-glucose was obtained. These facts confirm that the backbone of ganoderan consists of beta-1,3-linked D-glucopyranose residues.

From the fact that after mildly effecting Smith's degradation the glycerol (derived from the glucose residue at the non-reducing end) and erythritol (derived from the alpha-1,4-linked glucose residue) were both found in the water-soluble part, it was confirmed that 1,4-linkage is absent in the backbone.

These evidence elucidate that, unlike conventional antioncotic beta-1,3-glucans, ganoderan of the present invention is a novel glucan having side chains of beta-1,4-linked D-glucopyranose residues branched at the C-2 positions of the beta-1,3-linked D-glucopyranose residues in the backbone. These series of analyses clarified that the structure of ganoderan is composed of the repeating units as represented by the equation of

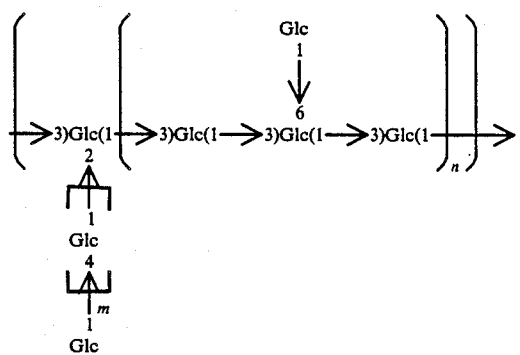

where Glc indicates the beta-linked D-glucopyranose residues; n, an integer from 3 up to 20; and m, an integer from 1 up to 3.

Also, the structure of the polyol-type ganoderan, obtained by first oxidizing ganoderan with periodic acid or its water-soluble salt, then reducing the resultant to convert, principally, the D-glucopyranose residues in the side chains into poly-alcohol, is a polyol-type beta-glucan having a backbone of repeating beta-1,3-linked glycopyranose residues represented by the equation of

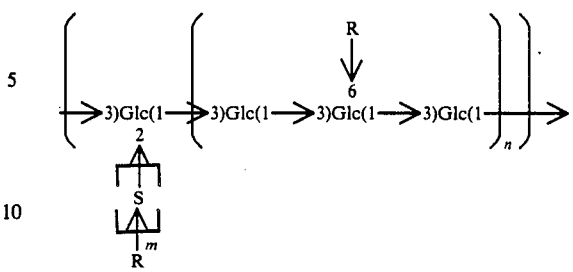

where Glc indicates the beta-linked D-glucopyranose residues; n, an integer from 3 up to 20; m, an integer from 1 up to 3; R,

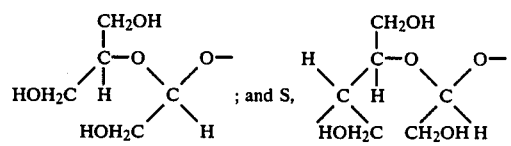

The average molecular weight of the intact- and polyol-type ganoderans can be freely adjusted in the range of about 100,000–10,000,000 by controlling the cultivation conditions of a Ganoderma microorganism, and/or conditions of the hydrolysis using hydrochloric acid, sulfuric acid, etc.

Ganoderan can be produced by inoculating and culturing a microorganism of Basidiomycetes, Aphyllophorales, Polyporaceae, Ganoderma, e.g. *Ganoderma lucidum* IFO 4912 and IFO 8346, and *Ganoderma japonicum* Lloyd, called as "mannen-take" or "reishi"; *Ganoderma applanatum* IFO 6498 and IFO 6499, called as "kofuki-saru-no-koshikake"; and *Ganoderma oregonense* Murril ATCC 14785, on a solid- or liquid-culture medium containing appropriate nutrients, such as carbon source, nitrogen source and mineral, etc., under still standing or aeration-agitation conditions to produce ganoderan in the culture, and recovering the ganoderan.

Any nutrient can be used as long as the culture medium containing the nutrient produces ganoderan. Examples of carbon source are glycerol, xylose, glucose, sorbitol, fructose, maltose, isomaltose, maltitol, sucrose, lactose, cellobiose, maltotriose, maltotetraose, starch hydrolysates having a Dextrose Equivalent (DE) in the range of 10–70, and molasses. Examples of nitrogen source are synthetic chemical compounds such as nitrates, ammonium salts, and ureas, and natural organic sources such as polypeptone, yeast extract, malt extract, corn steep liquor, defatted soybean extract, peptides, and amino acids. Phosphates, potassium salts, sulfates, magnesium salts, if necessary, iron salts, manganese salts, and calcium salts are feasible as mineral. The pH level in the culture medium is generally 4.0–9.0; and the temperature is 15°–35° C., ranges which allow the microorganism to grow and produce ganoderan. The microorganism may be cultured until maximum ganoderan production is obtained. Generally, ganoderan production reaches maximum in 3–20 days when cultured under aeration-agitation conditions. A liquid culture containing the accumulation of ganoderan is a highly viscous liquid. To a solid culture containing an accumulated ganoderan is added cold- or hot-water to obtain a similar viscous liquid.

To remove solids such as mycelia, these liquids may be treated with a suitable procedure, e.g. filtration, centrifugation, etc., and the resultant transparent filtrate or supernatant is recovered. The mycelia may be subjected to extraction using hot water or a dilute acid or alkali. The ganoderan containing liquid so obtained may be concentrated, cooled, and precipitated by, desirably, freeze-thawing method or by a method using an appropriate precipitant, e.g. methanol, ethanol, isopropanol or acetone, to form ganoderan as white sediment. A crude ganoderan can be separated from the sediment with a suitable procedure, e.g. filtration, centrifugation, etc. The ganoderan so obtained may be dissolved in water by heating, purified by repeatedly subjecting it to the above-described precipitation or by decoloring and deionizing with activated carbon and ion exchange, concentrated into syrup, dried, and pulverized to obtain a ganoderan powder with ease. In the step of drying, forced draft air drying, hot-air drying, spray-drying, drum drying and freeze-drying are feasible.

In order to produce the polyol-type ganoderan from the intact ganoderan thus obtained, one part of the intact ganoderan is suspended or dissolved in about 50–500 parts of an aqueous solution containing about 0.01–0.5M periodic acid or its water-soluble salt, e.g. sodium metaperiodate or potassium metaperiodate, and subjected to oxidation reaction at a pH, generally, in the range of 3–8. Preferably, this process should be carried out under mild conditions, e.g. in a dark place below room temperature, desirably below 15° C., so that the oxidation reaction is completed in 1–5 days.

Since the resultant polyol-type ganoderan wherein the side chains are principally oxidized is very reactive, it can be favorably used as, e.g. a support for immobilizing an enzyme by covalent linkage.

In order to reduce the polyol-type ganoderan, the oxidized mixture is first added with ethylene glycol or dialyzed to consume or remove the residual periodic acid, then added with a reductant. The polyol-type ganoderan may be recovered from the oxidized mixture, prior to the reduction.

Feasible reduction procedures are those which reduce the ganoderan oxidant. For example, hydrogenation using nickel catalyst and hydride reduction using sodium borohydride are suitable. The reduction mixture is then treated in usual manner to remove the nickel catalyst, or added with an organic acid to decompose the residual sodium borohydride, after which the resultant is purified by repeatedly precipitating it with an organic precipitant from an aqueous solution similarly as in the case of intact ganoderan or by decoloring and deionizing it with activated carbon and ion exchange, concentrated into syrup, dried, and pulverized to obtain a polyol-type ganoderan in powder with ease.

The intact- and polyol-type ganoderans thus obtained are feasible in various uses, e.g. in the chemical-, food-, pharmaceutical-, and other industries.

In the chemical industry, ganoderan may be used alone or in combination with other material(s) to manufacture compositions or molded articles, e.g. paste, viscosity-imparting agent, emulsion, powder, granule, thread, cloth, film, sheet, coating membrane, capsule and tablet, by taking advantage of their water-solubility and high molecular weight.

In the food industry, ganoderan may be incorporated in food products in general in order to impart to them with an appropriate viscosity, as well as to obtain a stabilized dispersion, gel formation and flavor locking, by taking advantage of their tastelessness, odorlessness, non-toxicity, water-solubility and high molecular weight. Since ganoderan is edible, but non-or scarcely digestable, hypocholesterolemic, and stimulates the excretion of heavy metals from the body, it can be favorably used as an ingredient for health foods.

Ganoderan can be used in pharmaceuticals. We found that ganoderan activates the cellular immune system and exhibits a strong antioncotic effect. Ganoderan can be favorably used as antioncotic. Particularly, intact ganoderan, polyol-type ganoderans and their mixture can be favorably used alone or together with pharmaceutically-acceptable agent(s), such as antioncotic, in the treatment of malignant tumors, e.g. breast cancer, lung cancer, bladder cancer, uterine cancer, colon carcinoma, gastric cancer, leukemia, lymphoma and skin carcinoma, to which intact- and/or polyol-type ganoderan is effective.

The following experiments will further clarify the antioncotic effect, toxicity, instructions, and dosage of the intact- and polyol-type ganoderans.

EXPERIMENT 1

Two groups of four-week old female ICR-JCL mice, each of ten mice, were implanted in their right groin area with an ascites tumor line, Sarcoma 180, in a dose of about $6 \times 10^6$ cells/mouse. One day after the implantation, mice were injected intraperitoneally every day with 0.1 ml of saline containing either a ganoderan, obtained by the method in Example 1, or a polyol-type ganoderan, obtained by the method in Example 3, in a dose of 1 mg/kg, 5 mg/kg or 10 mg/kg for 10 days. The control group was administrated similarly as above with ganoderan-free saline. On the thirty-fifth fifth day following the implantation, the mice were dissected, and the tumor masses were extracted and weighed. By comparing the tumor weights of the group administrated with the intact- or polyol-type ganoderan to those of the control, the tumor-inhibition ratios (%) were obtained.

$$\text{Tumor-inhibition (\%)} = \frac{(A - B)}{A} \times 100$$

where A indicates the average tumor weight of the ten control mice; and B, that of the ten mice successively administrated with either intact- or polyol-type ganoderan.

The results are listed in Table 1.

TABLE I

| Glucan | Dosage (mg/kg/day × times) | Average weight of tumor (g) | Tumor-inhibition ratio (%) | Complete regression | Remark |
|---|---|---|---|---|---|
| | 0 × 10 × 1 | 9.4 ± 1.4 | — | 0 | control |
| Ganoderan | 1 × 10 × 1 | 2.8 ± 1.5 | 70.2 | 3 | present invention |
| | 5 × 10 × 1 | 0.8 ± 0.7 | 91.5 | 8 | present invention |
| | 10 × 10 × 1 | 0.2 | 97.9 | 9 | present invention |
| Polyol-type ganoderan | 1 × 10 × 1 | 2.3 ± 1.2 | 75.6 | 5 | present invention |
| | 5 × 10 × 1 | 0.6 ± 0.5 | 93.6 | 8 | present invention |
| | 10 × 10 × 1 | 0.2 | 97.9 | 9 | present invention |

TABLE I-continued

| Glucan | Dosage (mg/kg/day × times) | Average weight of tumor (g) | Tumor-inhibition ratio (%) | Complete regression | Remark |
|---|---|---|---|---|---|
| · | 50 × 10 × 1 | 0 | 100 | 10 | present invention |

As is evident from the results in Table I, the intact- and polyol-type ganoderans of the invention are very effective in the inhibition of malignant tumor growth.

The validity of this experiment has been established in other warm-blooded animals, e.g. human, cow, horse, dog, cat, rabbit, rat, etc., and fowls, e.g. chicken, pigeon, etc.

EXPERIMENT 2

Two groups of 10 male $BDF_1$ mice, about 25 g each, were sub-cutaneously implanted in their dorsum area with 2 mm squares of Lewis' lung carcinoma tissue. From the eighth day following the implantation, the mice were injected intravenously twice every day with 0.1 ml of saline containing either an intact ganoderan, obtained by the method in Example 2, or a polyol-type ganoderan, obtained by the method in Example 3, in a dose of 0.02 mg/kg, 0.1 mg/kg or 1 mg/kg for 10 days. The control group was administrated similarly as above with ganoderan-free saline. On the twenty-third day following the implantation, the mice were dissected, and the resultant tumor masses were extracted and weighted. The tumor-inhibition ratios, obtained similarly as in Experiment 1, are listed in Table II.

TABLE I

| Glucan | Dosage (mg/kg/day × times) | Average tumor weight (g) | Tumor-inhibition (%) | Remark |
|---|---|---|---|---|
| | 0 × 10 × 2 | 8.2 ± 0.4 | — | * |
| Ganoderan | 0.02 × 10 × 2 | 6.0 ± 0.5 | 26.8 | ** |
| | 0.1 × 10 × 2 | 5.3 ± 0.7 | 35.4 | ** |
| | 1 × 10 × 2 | 4.0 ± 0.4 | 51.2 | ** |
| Polyol-type ganoderan | 0.02 × 10 × 2 | 5.8 ± 0.6 | 29.3 | ** |
| | 0.1 × 10 × 2 | 4.4 ± 0.7 | 46.3 | ** |
| | 1 × 10 × 2 | 3.2 ± 0.4 | 61.0 | ** |

Note:
*indicates the control; and **, the present invention.

As is evident from the results in Table II, the intact- and polyol-type ganoderans of the present invention exhibit a remarkable growth-inhibitory effect on malignant tumors including lung carcinoma, treatments of which have been deemed very difficult.

EXPERIMENT 3

An acute toxicity test was carried out in usual way by administrating orally, intraperitioneally or subcutaneously either an intact ganoderan, obtained by the method in Example 1, or a polyol-type ganoderan, obtained by the method in Example 3, to four-week old mice.

The results confirmed that the toxicity of both beta-glucans are very low: Their maximum administrable doses were not lethal. The $LD_{50}$ of these beta-glucans were estimated, not necessarily accurate, as 20 g/kg or higher on oral administration; 5 g/kg or higher, on intraperitoneal administration; and 1.5 g/kg or higher, on intravenous administration.

These experimental evidences confirm that the administration of intact- and polyol-type ganoderan is deemed to be very safe from the viewpoints of their effective doses, and the ganoderans can be, therefore, favorably used in the treatment of malignant tumors. They may be administered in any way as long as malignant tumors are treated thereby. For example, subcutaneous-, intramuscular-, intraperitoneal- and intravenous-injections, oral administration, administration in the form of suppository, external application, and instillation are feasible.

The daily dose of the intact- and polyol-type ganoderans for adult is generally from 0.1 mg to 500 g, varying in relation to the route of administration: for example, oral administration, from 10 mg/day up to 500 g/day; and for injection, from 0.1 mg/day up to 100 g per/day.

The invention will be more clearly understood with reference to the following examples.

EXAMPLE 1

Ganoderan

A liquid culture medium consisting of 5 w/v % glucose, 0.4 w/v % malt extract, 0.1 w/v % yeast extract, 0.05 w/v % $KH_2PO_4$, 0.05 w/v % $MgSO_4.7H_2O$ and water was sterilized at 120° C. for 20 minutes, and cooled, and the initial pH was adjusted to 6.6. A seed culture of *Ganoderma lucidum* IFO 4912 was inoculated on the liquid culture medium, and cultured at 27° C. for 8 days under aeration-agitation conditions.

The resultant culture was centrifuged at 7,000×g for 20 minutes to remove the mycelia. The resultant transparent supernatant was added with three volumes of ethanol under stirring to obtain a white featherlike crude ganoderan in the yield of about 15 g/10 liters of the culture. One g of the crude ganoderan was added with 500 ml water, dissolved to homogeneity, stirred gently, allowed to stand at 4° C. overnight, and centrifuged, after which the sediment was washed sufficiently with water, air-dried, and pulverized to obtain 750 mg of a white ganoderan powder.

This powder can be favorably used for various uses, e.g. in chemicals, food products, pharmaceuticals, etc.

The dried ganoderan (scarcely water-soluble) was stirred in 2N caustic soda under nitrogen atmosphere to prepare a 0.8% ganoderan solution. The solution was diluted with water to obtain 0.5N caustic soda solution whose specific rotation $[\alpha]_D^{25}$ was about plus ten degrees.

Separately, the solution was dialyzed against water with cellophane membrane to obtain a caustic soda-free homogenous ganoderan solution wherein no sedimentation was noted.

EXAMPLE 2

Ganoderan

A liquid culture medium consisting of 6 w/v % partial starch hydrolysate (syrup solid, DE 30), 0.2 w/v % wheat germ, 0.3 w/v % corn steep liquor, 0.1 w/v % $NH_4NO_3$, 0.1 w/v % $K_2HPO_4$, 0.05 w/v % $MgSO_4.7H_2O$, 0.05 w/v % KCl, 0.0001 w/v % $MnSO_4.4H_2O$ and water, sterilized at 120° C. for 20 minutes, and cooled, and the initial pH was adjusted to 6.2. A seed culture of *Ganoderma applanatum* IFO 6498 was inoculated on the culture medium, and cultured at 30° C. for 6 days under aeration-agitation conditions.

The resultant culture was treated similarly as in Example 1 to obtain a crude ganoderan in the yield of about 28 g/10 liters of the culture.

One g of the crude ganoderan was dissolved in 400 ml water by heating, cooled, freezed, melted, and centrifuged, after which the sediment was washed sufficiently with water, freeze-dried, and pulverized to obtain about 700 mg of a white ganoderan powder.

This powder can be favorably used for various uses, and compares well with that at Example 1.

EXAMPLE 3

Polyol-type ganoderan

Ten g of a ganoderan, obtained by the method in Example 1, was suspended in 500 ml of a solution containing 6.6 g of sodium metaperiodate, and then allowed to stand in a dark place at 10° C. for 7 days to effect oxidation reaction. The reaction mixture was dialyzed against water, added with 1.5 g sodium borohydride, allowed to stand at room temperature for two days to effect reduction reaction, added with acetic acid to bring its pH 6.0 and also to decompose the residual sodium borohydride, and dialyzed against water.

Thereafter, the reaction mixture was added with three volumes of methanol, and centrifuged to recover the resultant sediment which was then dissolved in water, precipitated, dissolved again in water, freeze-dried, and pulverized to obtain about 7.4 g of a white powder of polyol-type ganoderan.

This powder is excellently water-soluble, and favorably usable in various uses, e.g. in chemicals, food products, pharmaceuticals, etc.

EXAMPLE 4

Film

A 10 w/v % solution containing a ganoderan, obtained by the method in Example 1, and 10 w/v % glycerine on the basis of ganoderan solid was casted on the surface of a glass plate, and dried in a current of 70° C. air to obtain a transparent film having a satisfiable tensile strength.

This film is glossy, and excellent in transparency and tensile strength. This film has a high gas-barrier ability, and is, therefore, low in oxygen-permeability. Thus, it can be favorably used to coat or seal a variety of products which are susceptive to oxidation to extremely extend their shelf lives.

EXAMPLE 5

Fiber

A material solution containing 20 w/v % of a polyol-type ganoderan, obtained by the method in Example 3, was heated to 80° C., extruded into air through a cylindrical nozzle, 0.3 mm in diameter and 1 mm in length, at room temperature by applying a slightly high pressure (3 kg/cm$^2$) to form a strand, and the strand was rolled round a reel while transpiring and drying the moisture. The fiber thus obtained was about 20 μ thick and excellent in tensile strength.

Since the fiber is twistable, knittable, weaveable, hydrophilic, non-toxic, and non-irritative to the skin, it can be favorably used for, e.g. sanitary cotton, sanitary napkin, gauze, suture, etc. The fiber may be embedded in the body to treat malignant tumor, after shaped into desirable form. Blended fiber may be used for clothing such as underwears by taking advantage of the moisture absorbability, non-charging ability and dyeability.

EXAMPLE 6

Coating membrane

A 0.5 w/v % aqueous solution of a ganoderan, obtained by the method in Example 2, was heated to 35° C. Within 10 hours after laying, fresh eggs were dipped in the solution for 30 minutes, and dried in a current of 30° C. air to form a coating membrane on their surfaces. The eggs were then stored at room temperature (15°–25° C.), and their shelf lives were compared with those of uncoated eggs. The coating membrane extended the shelf lives about 5–10-folds.

EXAMPLE 7

Cup

A ganoderan powder, obtained by the method in Example 1, was sprayed with water under stirring to bring its moisture content to about 30 w/w %, and prepared into strand with an extrusion molding machine. The strand was cut into pellets, 2.5 mm in diameter and 4 mm in length, which were then transferred into an injection molding machine, and injected into metal mold at a resin temperature of 120° C. to obtain a translucent cup having a desirable tensile strength.

EXAMPLE 8

Fertilizer rod

Seventy parts of a compound fertilizer (N=14%, $P_2O_5$=8%, $K_2O$=12%), 10 parts of a crude ganoderan obtained by the method in Example 1, 15 parts of calcium sulfate, and 5 parts of water were admixed, and heated to 80° C. with an extruder, L/D=20, compression ratio=1.8, bore=30 mm, to obtain a fertilizer rod.

This fertilizer rod is easily handleable, and does not necessarily require special packaging. The mechanical strength of the product is appropriate for deep placement, and the elution rate of the fertilizer elements can be regulated by employing different formulations.

EXAMPLE 9

Capsule

An aqueous solution containing 10 w/v % of a ganoderan, obtained by the method in Example 2, and 10 w/v % of gelatine was heated to 60° C., and dearated, after which metal rods were dipped in the solution, immediately pulled out, and gradually dried in a current of 40° C. air to obtain a high-quality glossy hard capsule having a desirable transparency and an elasticity.

This capsule is suitable as a container for encapsulating a dose of a suppository or a medicine for oral administration.

EXAMPLE 10

Adhesive

A mixture of 30 parts of dimethyl sulfoxide, 25 parts of water, 2 parts of a ganoderan obtained by the method in Example 2, 8 parts of pullulan and 2 parts of dibenzylidenexylitol was dissolved by stirring at 90° C. for one hour, and injected in different cylindrical lipstick-type containers, 14 mm in diameter, 50 mm in length and equipped with an up- and down-movement mechanism, and cooled at room temperature to produce a solid adhesive.

This adhesive was thinly extended on a kraft paper in a uniform thickness, and the initial adhesive strength was satisfiable.

EXAMPLE 11

Alimentary pastes

Seventy parts of rice powder, 20 parts of potato starch, 10 parts by weight of wheat flour, 2 parts of a ganoderan obtained by the method in Example 1, and 40 parts of 10% saline solution were mixed, heated with steam, and kneaded to obtain a dough, which was then allowed to stand overnight, stripped, and heated in boiled water for three minutes to obtain a cooked alimentary pastes having a satisfiable stickiness.

EXAMPLE 12

"CHINMI"

Thirty parts of a minced chicken was parched on a frying pan together with 2 parts of sucrose, 2 parts of soy sauce and 6 parts of "MIRIN" (an alcoholic seasoning), admixed with 3 parts of a ganoderan obtained by the method in Example 1, heated, and compressed at about 150°–170° C. and a slightly high pressure (about 50 kg/cm$^2$) to obtain a sheet of about 1 cm thick. The sheet was cut into strips of adequate size to obtain "CHINMI"—a type of dehydrated food.

The product is suitable as relish or snack food for children.

EXAMPLE 13

Fish meat product

Four thousand parts of a thawed raw meat paste of Alaska pollack was mixed with 80 parts of maltose, 80 parts of sodium glutamate, 200 parts of potato starch, 300 parts of ice water, 12 parts of sodium tripolyphosphate, 120 parts of salt, and 100 parts of an aqueous solution containing 10 parts of a polyol-type ganoderan obtained by the method in Example 3, and 1 part of sorbitol, after which about 120 g aliquots of the mixture were shaped, and placed on pieces of wood. The resultant was heated with steam so that the product temperature increased to about 80° C. in 30 minutes, cooled at room temperature, and allowed to stand at 4° C. for 24 hours to obtain a fish meat product.

The product was excellent in gloss and biting properties, as well as having a desirable elasticity and a silky appearance.

EXAMPLE 14

Batter flour

A batter flour consisting of one hundred parts of soft flour and 1 part of a ganoderan obtained by the method in Example 2 was admixed with 300 parts of water by stirring to obtain a coating solution. Raw fishes and vegetables, such as lobster and sweet potato slices, were coated, and fried.

This batter flour was palatable and excellent in stickiness.

EXAMPLE 15

Ice cream

Seventy parts of 40 w/w % cream, 200 parts of whole sweetened condensed milk, 460 parts of whole milk, 20 parts of defatted milk powder, 5 parts of sucrose, 5 parts of maltose, and 4 parts of 5% aqueous solution of a ganoderan obtained by the method in Example 2 were mixed by heating, pasteurized at 70° C. for 30 minutes, passed through a homogenizer, immediately cooled to 3°–4° C., aged overnight, and placed in a freezer to obtain a smooth, tasty ice cream.

EXAMPLE 16

Lemon jelly

Three parts of agar and 5 parts of a polyol-type ganoderan obtained by the method in Example 3 were dissolved with 200 parts of water and 50 parts of sucrose, and cooled to 65° C. The mixture was added with 350 parts of carbonated water containing small amounts of flavors including lemon flavor, placed in a mold, and cooled to obtain a glossy lemon jelly.

This jelly is a health food containing ganoderan, a dietary fiber.

EXAMPLE 17

Yoghurt

One hundred and seventy-five parts of defatted milk powder, 80 parts of sucrose, 50 parts of maltose, and 30 parts of a ganoderan obtained by the method in Example 1 were dissolved in 1,200 parts of water, homogenized, pasteurized at 80° C. for 30 minutes, and cooled to 40° C., after which the mixture was inoculated with 30 parts of a starter prepared from Lactobacillus microorganism in a commercialized yoghurt product, and fermented at 37° C. for 8 hours to obtain a yoghurt gel.

This yoghurt was tasty, glossy, and smooth to the palate. This ganoderan containing jelly is a health food having hypocholesterolemic activity.

EXAMPLE 18

Tablet

One hundred parts of 20 w/v % aqueous solution of a polyol-type ganoderan obtained by the method in Example 3 was added with 140 parts of maltose and 20 parts of vitamin A palmitate, mixed by stirring, casted on the surface of a glass plate, air-dried, pulverized, and shaped into tablet in usual way.

This tablet contained one hundred thousand IU of vitamin A palmitate/g, and scarcely lost its activity on 3-month standing at 30° C. It can be favorably used as antioncotic for oral administration in the treatment of malignant tumors, e.g. gastric cancer, duodenal cancer, rectum cancer, etc.

EXAMPLE 19

Tablet

Fifty parts of 2-(acetyloxy) benzoic acid was admixed with 14 parts of a ganoderan obtained by the method in Example 1 and 4 parts of cornstarch, and shaped into tablet with conventional tablet machine.

The resultant tablet was non-hygroscopic and excellent in physical strength and degradability in water.

EXAMPLE 20

Injection

A 3 w/v % aqueous solution of a ganoderan, obtained by the method in Example 1, was purified by decoloration using activated carbon and deionization using ion exchange resins of H- and OH-forms, concentrated in vacuo, and filtered with a membrane filter under sterile conditions. The filtrate so obtained was distributed in sterilized 2 ml-vials to give a ganoderan content of 200 mg/vial, and freeze-dried. The vials were then sealed to obtain an injection.

The content in the vials is dissolved or suspended in saline, prior to subcutaneous- or intramuscular-injection. This injection can be favorably used in the treatment of malignant tumors, e.g. breast cancer, lung carcinoma, liver carcinoma, leukemia, etc.

EXAMPLE 21

Injection

An about 5 w/v % aqueous solution of a polyol-type ganoderan, obtained by the method in Example 3, was purified by decoloration using activated carbon and deionization using ion exchange resins similarly as in Example 20, concentrated, and filtered with a membrane filter under sterile conditions, after which the concentration of the filtrate was adjusted to obtain an isotonic solution containing 5 w/v % ganoderan. The solution was distributed in 20 ml-vials, and sterilized to obtain an injection.

This injection can be favorably used for intraperitoneal- or intravenous-injection in the treatment of malignant tumors, e.g. breast cancer, bladder cancer, cancer of the endometerium, colon carcinoma, gastric cancer, etc.

EXAMPLE 22

Ointment

A ganoderan powder, obtained by the method in Example 2, was admixed first with a small amount of liquid petrolatum, then with petrolate to obtain an ointment having a ganoderan content of 10 mg/g.

This ointment can be favorably used in the treatment of malignant tumors, e.g. skin carcinoma, breast cancer, lymphoma, etc.

While the described embodiments represent the preferred forms of the present invention, it is to be understood that modifications will occur to those skilled in the art without departing from the spirit of the invention. The scope of the invention is therefore to be determined solely by the appended claims.

We claim:

1. A beta-glucan having a molecular weight in the range of 100,000–10,000,000 comprising repeating units as represented by the following formula:

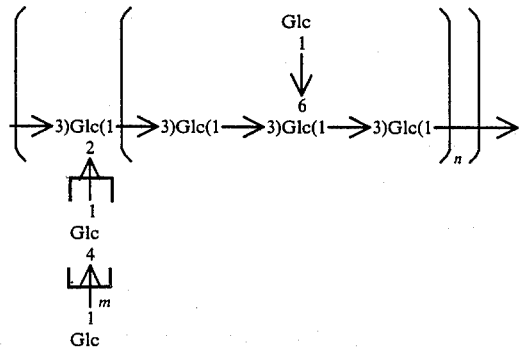

where Glc indicates beta-linked D-glucopyranose residues; n, an integer from 3 up to 20; and m, an integer from 1 up to 3.

2. A polyol-type beta-glucan having a molecular weight in the range of 100,000–10,000,000 comprising repeating units as represented by the following formula:

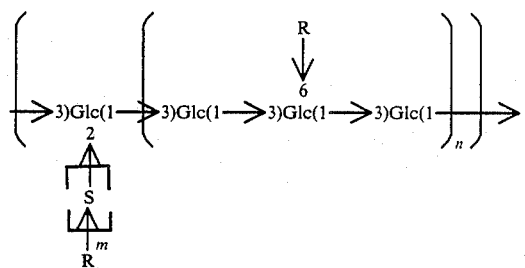

where Glc indicates beta-linked D-glucopyranose residues; n, an integer from 3 up to 20; m, an integer from 1 up to 3; R,

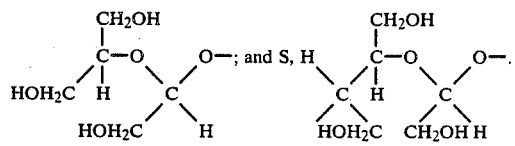

3. A molded article, containing a member selected from the group consisting of a beta-glucan having a molecular weight in the range of 100,000–10,000,000 comprising repeating units as represented by the following formula:

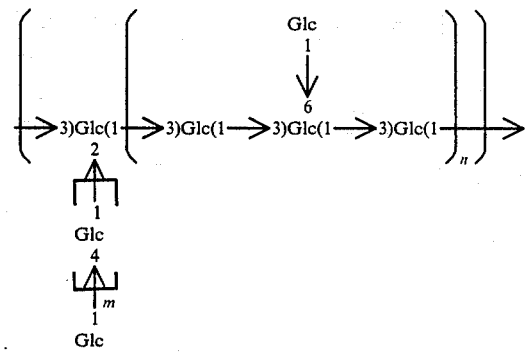

where Glc indicates beta-linked D-glucopyranose residues; n, an integer from 3 up to 20; and m, an integer from 1 up to 3; and a polyol-type beta-glucan having a molecular weight in the range of 100,000–10,000,000 comprising repeating units as represented by the following formula:

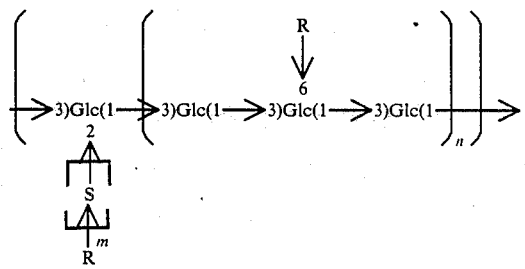

where Glc indicates beta-linked D-glucopyranose residuces; n, an integer from 3 up to 20; m, an integer 1 up to 3; R,
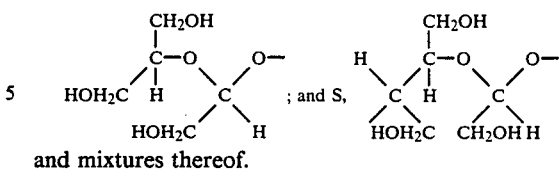
and mixtures thereof.
* * * * *